United States Patent
Platt et al.

(10) Patent No.: US 10,553,413 B2
(45) Date of Patent: Feb. 4, 2020

(54) MASS SPECTROMETER

(71) Applicant: Micromass UK Limited, Wilmslow, Cheshire (GB)

(72) Inventors: Stephen John Platt, Cheshire (GB); Keith George Richardson, Derbyshire (GB); David Darrell Williams, Wilmslow (GB); Richard Denny, Staffordshire (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/957,464

(22) Filed: Apr. 19, 2018

(65) Prior Publication Data
US 2018/0308673 A1   Oct. 25, 2018

Related U.S. Application Data

(63) Continuation of application No. 15/231,155, filed on Aug. 8, 2016, now Pat. No. 9,953,814, which is a
(Continued)

(30) Foreign Application Priority Data

Mar. 30, 2012   (GB) .................................. 1205805.3

(51) Int. Cl.
*H01J 49/02*   (2006.01)
*H01J 49/00*   (2006.01)
(Continued)

(52) U.S. Cl.
CPC ........ *H01J 49/0036* (2013.01); *G01N 27/622* (2013.01); *H01J 49/022* (2013.01);
(Continued)

(58) Field of Classification Search
CPC ............... H01J 49/0027; H01J 49/0031; H01J 49/0036; H01J 49/022; H01J 49/40;
(Continued)

(56) References Cited

U.S. PATENT DOCUMENTS 5,995,989 A * 11/1999 Gedcke ............... H01J 49/0036
708/203
6,253,162 B1 * 6/2001 Jarman ............... H01J 49/0036
250/282
(Continued)

FOREIGN PATENT DOCUMENTS

CA   2537328 A1   4/2005
WO   2010136775 A2   12/2010

*Primary Examiner* — David E Smith
(74) *Attorney, Agent, or Firm* — Womble Bond Dickinson (US) LLP; Deborah M. Vernon; Heath T. Misley

(57) ABSTRACT

A hardware module which operatively carries out a method of compressing mass spectral data, the method comprising: receiving a first signal output from an ion detector of a mass spectrometer; processing the first signal to a digital signal at an output being data frame types representative of the first signal output; temporarily storing the data frame types in a memory block and reading a data frame from the memory block and determining its data frame type and according to its data frame type compressing the data frame according to one or more compression algorithms to generate a compressed data output stream.

18 Claims, 12 Drawing Sheets

Related U.S. Application Data continuation of application No. 14/389,635, filed as application No. PCT/GB2013/050831 on Mar. 28, 2013, now Pat. No. 9,412,570.

(51) Int. Cl.
*H01J 49/40* (2006.01)
*H03M 1/12* (2006.01)
*H03M 7/30* (2006.01)
*H03M 7/40* (2006.01)
*G01N 27/62* (2006.01)

(52) U.S. Cl.
CPC ............... *H01J 49/40* (2013.01); *H03M 1/12* (2013.01); *H03M 7/3084* (2013.01); *H03M 7/40* (2013.01)

(58) Field of Classification Search
CPC .... G01N 27/622; H03M 1/12; H03M 7/3084; H03M 7/40
See application file for complete search history.

(56) References Cited

U.S. PATENT DOCUMENTS

| | | | |
|---|---|---|---|
| 7,365,309 B2 | 4/2008 | Denny et al. | |
| 8,004,432 B2 | 8/2011 | Kawato | |
| 9,412,570 B2 | 8/2016 | Platt et al. | |
| 2007/0114379 A1* | 5/2007 | Roushall | H01J 49/0036 250/284 |
| 2008/0103710 A1* | 5/2008 | Wegener | G01R 13/029 702/66 |
| 2008/0270083 A1* | 10/2008 | Lange | G06K 9/00523 702/193 |
| 2010/0309031 A1* | 12/2010 | Kawato | H01J 49/0036 341/87 |
| 2012/0133532 A1* | 5/2012 | Hunt | H03M 7/30 341/87 |
| 2012/0136586 A1* | 5/2012 | Spreadbury | H01J 49/0036 702/23 |
| 2012/0228488 A1* | 9/2012 | Decker | H01J 49/0036 250/282 |

* cited by examiner

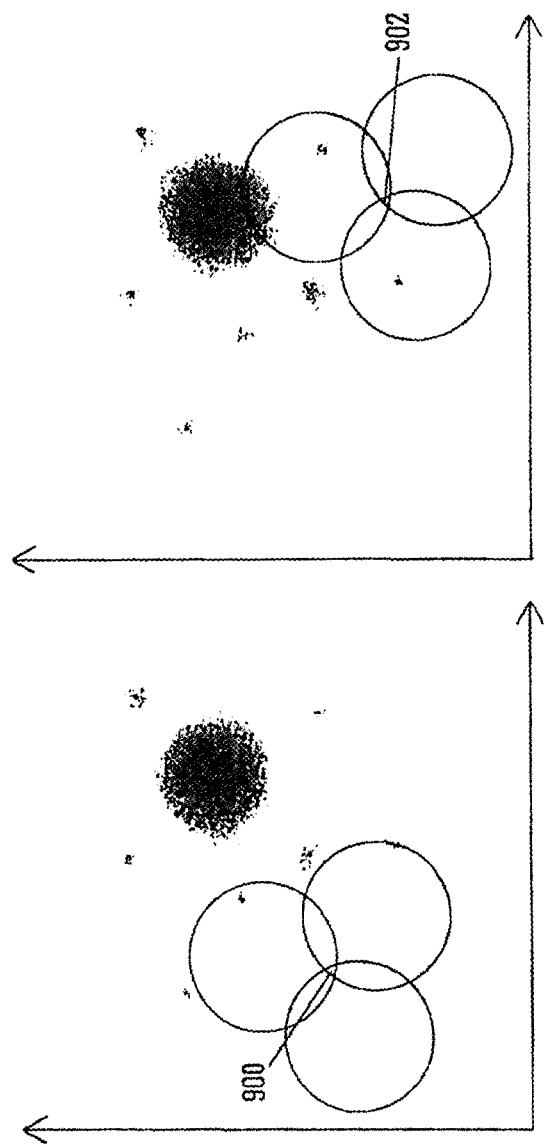

MASS SPECTROMETER

CROSS REFERENCE TO RELATED APPLICATIONS

This application is a continuation of U.S. patent application Ser. No. 15/231,155, filed 8 Aug. 2016, which will issue as U.S. Pat. No. 9,953,814 on 24 Apr. 2018, which is a continuation of U.S. patent application Ser. No. 14/389,635, filed 30 Sep. 2014, which is the National Stage of International Application No. PCT/GB2013/050831, filed 28 Mar. 2013, which claims priority from and the benefit of United Kingdom Patent Application No. 1205805.3 filed on 30 Mar. 2012. The entire contents of these applications is incorporated herein by reference.

BACKGROUND OF THE PRESENT INVENTION

The present invention relates to a mass spectrometer and a method of mass spectrometry. In some embodiments, the invention relates to a hardware module and method for acquiring and compressing mass spectral data, for example for onward analysis.

Mass spectral data is typically generated by the impact of ions on one or more ion detectors, which provide signals which can be processed to provide information as to the mass to charge (m/z) ratios and the number of ions (e.g. by the intensity of the ion count) at a particular m/z, the information typically being provided in the form of a mass spectrum. Mass spectra may be further analysed to elucidate structural information about the compounds analysed.

Modern mass spectrometers are capable of acquiring very large quantities of data as a result of both their sensitivities and the number of different forms of analysis they are able to perform on a single sample. For example, where, say, a tandem mass spectrometer such as a quadrupole time-of-flight mass spectrometer is coupled to a liquid chromatograph, the instrument may be capable of acquiring several thousand individual mass spectra for a single sample. These spectra result from the time-of-flight mass analyser obtaining up to several thousand spectra per second which may correspond to many m/z settings of the quadrupole mass analyser in turn from an array of residence times in the column of the liquid chromatograph.

Where an ion mobility spectrometer is also coupled to a system, for example between the liquid chromatograph and, say, a time-of-flight mass analyser, the number of spectra acquired increases again by virtue of the array of ion drift times which may be analysed in the mass analysers.

Furthermore, where the resolution of the mass analyser(s) is very fine, a correspondingly large number of m/z and intensity data require processing and storage.

In a typical mass spectrometer, such data is transferred to computer for processing. Indeed, it is typical for the data to be transferred to and through a series of computers, at least one of which may be within the instrument itself, where it may be subject to optional noise-reduction algorithms where periodic background noise is effectively filtered out from the mass spectral data as described in British patent application GB2409568. It is typical to store the data in one or more databases in one or more of the computers such that it can be searched and retrieved by users at a later date.

FIG. 1A shows a spectrometer system of the prior art e.g as disclosed in WO2010136775 which is also incorporated herein by reference, the system having an ion source 1, an acceleration region 2, a field-free region 3, a reflectron (ion mirror) 4, a detector 5, an acquisition system 6, an embedded computer system 7 and a host computer system 8.

Ions formed in the ion source from the sample compound enter the acceleration region where they are driven by an acceleration voltage pulse into the field-free region. The ions are accelerated to a velocity determined by the energy imparted by the acceleration pulse and their mass, lighter ions achieving a higher velocity.

A reflectron is used to increase the length of the path the ions take from the acceleration region to the detector for a given length of analyser housing. This allows greater separation in time between ions with different velocities.

Ions arrive at the detector after a time determined by their velocity and the distance traveled, thus enabling their mass to be determined.

The output of the detector is sampled by the acquisition system which then generates a mass spectrum that is passed to the embedded computer system. The operation of the acquisition system is described in greater detail below.

The embedded computer system passes the mass spectrum data to the host computer system for further analysis and storage. The embedded computer system can also analyse the data for data dependent acquisitions. This allows the content of the mass spectrum data to be used to change the mass spectrometer's configuration on a scan-by-scan basis.

FIG. 1B shows a block diagram of the acquisition system of the prior art comprising, an acquisition engine 9, a data throughput optimization module 19 and an Ethernet interface 11 for the output of data to the embedded computer system 7. The data throughput optimization block itself comprises a data compression engine 21, a ring buffer 13 and a hardware protocol stack 15.

The detector signal from the mass spectrometer that is input to the acquisition system is first sampled by a high speed analogue-to-digital converter (ADC) within the acquisition engine.

The acquisition engine then detects any peaks present within the signal and converts them useable information e.g. comprising of time and intensity.

The next stage of the optimization block is the data compression engine 21 that uses an LZRW3 (Lempel-Ziv Ross Williams) compression algorithm to provide data compression on the data from the data acquisition engine.

The output of the data compression engine is input into the ring buffer 13, whereby the ring buffer 13 formats the data and transmits it to a hardware protocol stack, which in turn transmits the data to a computer system for processing.

As the quantity of data that is collected increases, the speed of transfer of that data between devices and the speed of processing that data into usable forms is compromised. This represents a particular problem where data cannot be transferred and recorded onto a computer storage medium as fast as the mass spectrometer is able to acquire it. In such instances, data may be lost on an indiscriminate basis. Further problems arise in providing sufficient data storage space and in the processing power required for the one or more computers to provide the data in a usable and interpretable form.

The present invention seeks to address these problems by providing a hardware module and a method for compressing mass spectral data to increase the speed at which such data can be processed and transferred.

SUMMARY OF THE PRESENT INVENTION

In a first aspect, the invention provides a method for compressing mass spectral data, the method comprising:

receiving a first signal output from an ion detector; processing the first signal to a digital signal at an output being data frame types representative of the first signal output; temporarily storing the data frame types in a memory block and reading a data frame from the memory block and determining its data frame type and according to its data frame type compressing the data frame according to one or more compression algorithms to generate a compressed data output stream.

Preferably, the step of processing the first signal to a digital signal comprises using an analogue to digital converter to digitise the first signal.

Preferably, the first signal output is a voltage and/or representative of one or more ion arrival times and/or one or more ion intensities.

Preferably, the method includes determining an intensity distribution from a plurality of different regions or portions of mass spectral data; estimating a background intensity for one or more regions or portions of said mass spectral data or said mass spectrum from said intensity distribution; and adjusting the intensity of one or more regions or portions of said mass spectral data or said mass spectrum in order to remove or reduce the effects of said estimated background intensity. Preferably, the one or more compression algorithms include any one or more of:

(a) estimating the maximum intensity of a hypothetical mass spectral peak at a first data point by calculating the width of a real mass spectral peak of which the first data point forms a part, the width measured in a number n of data points; summing intensities of n second data points adjacent to said first data point; and discarding the first data point if the hypothetical mass spectral peak is beneath a predetermined threshold intensity;

(b) providing intensity information in respect of a first data point by calculating the difference between the intensity of the first data point and an intensity of a second data point adjacent the first data point;

(c) providing m/z information in respect of a first data point by calculating the difference between the mass index or m/z of the first data point and a mass index or m/z a second data point adjacent the first data point;

(d) allocating a fixed number p of bits to storage of the intensity information provided by (b) and/or the m/z information provided by (c), allocating overflow storage to store complete or higher order intensity and/or m/z information where said information is only partially storable in p bits.

(e) transforming intensity value in respect of a first data point to a square root of the received intensity value;

(f) selecting a data file format for recording the m/z of a data point dependent on the intensity of the data point and/or the width of a mass spectral peak of which said data point forms a part and/or noise characteristics at or around the data point, the file format selected from a plurality of file formats having varying file sizes;

(g) providing m/z information in respect of a first data point by calculating the difference between the mass index or m/z of the first data point and a mass index or m/z of a hypothetical mass spectral peak, e.g. an anchor point; and (h) performing further lossless compression, e.g. Lempel-Ziv and/or Huffman coding.

Preferably, for each data point, estimating a maximum intensity of a hypothetical mass spectral peak located at the data point using a theoretical expected profile and/or footprint of the mass spectral peak determined from expected characteristics of an instrument used to perform the method, flagging all data points with the footprint if the maximum intensity exceeds a predetermined threshold intensity; and, when all relevant data points have been processed, deleting any data points that have not been flagged.

Preferably, the method includes carrying out the sequence of (b), (c), (d) and (h).

Preferably, the method includes carrying out the sequence of (a) and (h), preferably in combination with determining an intensity distribution from a plurality of different regions or portions of mass spectral data; estimating a background intensity for one or more regions or portions of said mass spectral data or said mass spectrum from said intensity distribution; and adjusting the intensity of one or more regions or portions of said mass spectral data or said mass spectrum in order to remove or reduce the effects of said estimated background intensity.

Preferably, the method is carried out in real time, e.g. before any data is recorded.

In a further aspect, the invention provides a method of mass spectrometry comprising a method of compressing data as described above.

In a further aspect, the invention provides a computer software program for implementing the method as described above.

In another aspect, the invention provides a carrier carrying processor control code to configure hardware to implement the method as described above.

In another aspect, the invention provides a hardware module configured to implement the method of compression.

In a further aspect, the invention provides a method for compressing mass spectral data, the method comprising estimating the maximum intensity of a hypothetical mass spectral peak at a first data point by calculating the width of a real mass spectral peak of which the first data point forms a part, the width measured in a number n of data points; summing intensities of n second data points adjacent to said first data point; and discarding the first data point if the hypothetical mass spectral peak is beneath a predetermined threshold intensity.

In a further aspect, the invention provides a method for compressing mass spectral data, the method comprising
(a) providing intensity information in respect of a first data point by calculating the difference between the intensity of the first data point and an intensity of a second data point adjacent the first data point; and/or
(b) providing m/z information in respect of a first data point by calculating the difference between the time of flight or m/z of the first data point and a time of flight or m/z of a second data point adjacent the first data point.

Preferably, the method further comprises allocating a fixed number p of bits to storage of the intensity information provided by (a) and/or the m/z information provided by (b), allocating overflow storage to store complete or higher order intensity and/or m/z information where said information is only partially storable in p bits.

In a further aspect, the invention provides a method of compressing mass spectral data, the method comprising transforming a received intensity value in respect of a first data point to a square root of the received intensity value.

In a further aspect, the invention provides a hardware module for compressing mass spectral data, the hardware module comprising: an input to receive input data being a first signal output from an ion detector, the data being characteristic of ion arrival times and/or ion intensities; an analogue to digital converter, to receive at an input the first signal and process the first signal to a digital signal; a first processor block, the first processor block having logic gates to receive the digitised first signal and process the first signal to data frame types representative of one or more ion arrival times and/or one or more ion intensities; a second processor block comprising a buffer having an input to receive the data frame types and a memory block to temporarily store the data frame types and an output coupled to a compression control logic block for reading a data frame from the memory block and for determining its data frame type and according to its data frame type compressing the data frame according to one or more compression algorithms to generate a compressed data output stream.

Preferably, the first processor block may comprise multiple processing blocks to allow parallel processing of the digitised first signal. Preferably, the second processor block may comprise a scan combine logic block for combining multiple data streams from the first processor block into a single data stream by summation and/or grouping of the intensity values. The compression control logic block may perform the compressing in real time, for example using a Field Programmable Gate Array ("FPGA") or a Graphical Processor Unit ("GPU").

BRIEF DESCRIPTION OF THE DRAWINGS

Embodiments of the invention will now be described, by way of example only, and with reference to the accompanying drawings of which:

FIGS. 10A and 10B are a schematic representation of part of a 2D dataset illustrating the "Data Sweep" method of data reduction.

DETAILED DESCRIPTION OF PREFERRED EMBODIMENTS

Figure 1A:
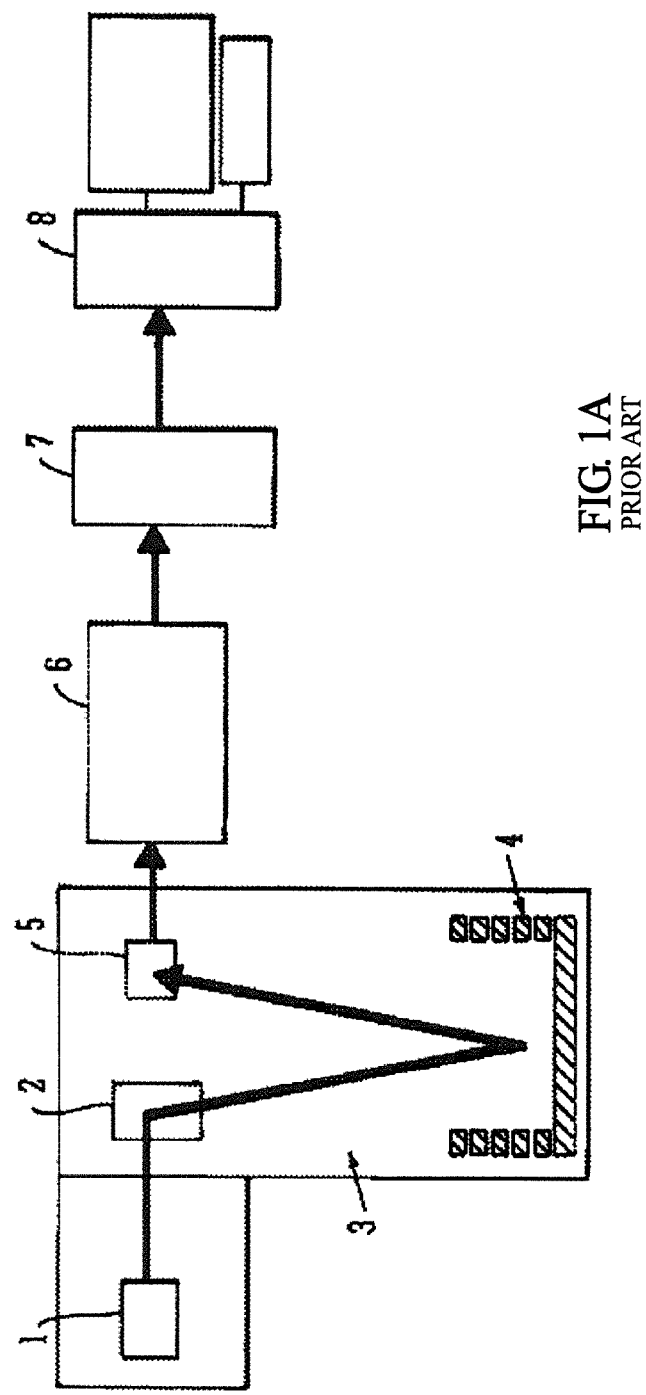
FIG. 1A shows a spectrometer system of the prior art in diagrammatic form.
Figure 1B:
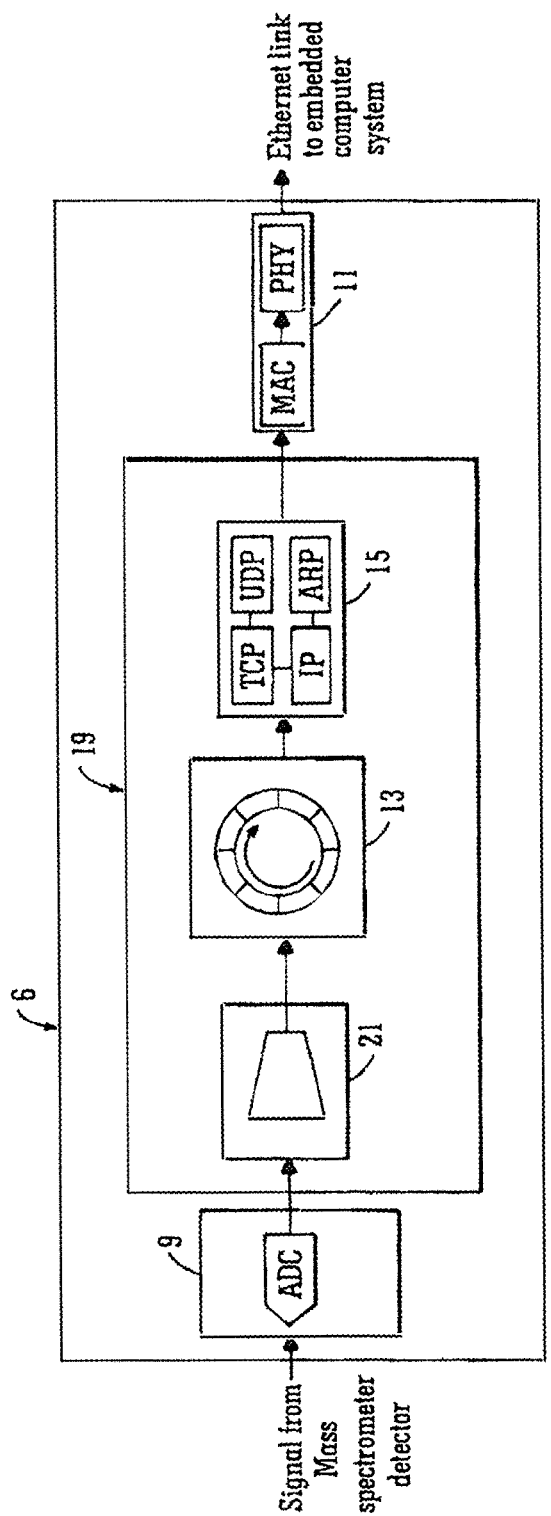
FIG. 1B shows a block diagram of a data optimization module within the acquisition system for the prior art spectrometer of FIG. 1A.

Increasing instrument sensitivity, detector dynamic range and the adoption of higher dimensional separation techniques all contribute to a continuing increase in the amount of data that can be produced by modern mass spectrometers. The following also describes a sequence of lossless and lossy compression steps tailored to mass spectral data that can be used in many combinations, in hardware or in software, to reduce the size of the datasets produced. Smaller datasets are also more convenient for long-term storage, transmission across networks and post-acquisition processing.

Implementation of the software implemented embodiments considers simultaneous compression of one or more mass spectra. A data point or record in a mass spectrum usually comprises of a mass (or arrival time) and intensity (signal) along with other information. Points with zero intensity (s=0) are typically discarded. While the description below focuses on mass and intensity, other quantities (including, but not limited to, saturation flags) may be treated in a similar way to intensity.

Broadly speaking, the following techniques can be applied to continuum data or to peak detected (spectrum by spectrum) data:

1) Background subtraction. Mass spectra may optionally be prepared for compression through the application of a background subtraction algorithm (such as described in GB2409568).

2) Adaptive thresholding. Given knowledge of local peak widths, the intensity (or maximum possible intensity) of a hypothetical peak at a given position in a multi-dimensional dataset is estimated. If this calculation is performed at a sufficiently dense number of locations in the data, data points which could never contribute to a hypothetical peak exceeding some predetermined local threshold intensity may be discarded. The local threshold intensity may vary with position in the data. The method may be employed in datasets of any dimensionality.

3) Intensity differentiation. Intensities in adjacent channels in a mass spectrum are often correlated, especially across a peak. More specifically the absolute value of $s(n)-s(n-1)$ is often much smaller than $s(n)$, resulting in fewer non-zero bits. $s(0)$ is stored directly.

4) Mass differentiation. In densely populated spectra, the differences between adjacent mass indices $m(n)-m(n-1)$ are often much smaller than the indices $m(n)$. In the limit in which all channels are populated, all of these differences are 1. $m(0)$ is stored directly. Again this results in fewer non-zero bits.

5) Packing of mass and or intensity differences. The number of bits allocated to store mass or intensity differences may be chosen such that a high proportion of data points can be stored without overflow. When overflows occur, additional records may be created to store either the full precision data or the truncated, higher order, bits. An indexing scheme is used to link the repairs to the data.

6) Transforming intensities given known noise distributions. When intensities are subject to Poisson statistics (common in mass spectrometry when intensities are ion counts), each intensity is subject to noise with a standard deviation equal to its square-root. However, the standard deviation of the square root of intensity is then simply $\sqrt{i}$, so it is sufficient to store square-root intensities with a fixed precision of around $\sqrt{i}$. Data may be pre-scaled so that it is more accurately described by Poisson statistics. Similarly, other intensity transformations may be used depending on the relevant noise distribution.

7) Limiting mass precision. For peak-detected data, the precision of a detected mass is related to the local peak width, the intensity and the properties of the noise. When these are known, the number of bits used to store the mass value may be limited accordingly. It can be useful to define several peak record formats having different precision. High precision mass anchor records may be followed by lower precision peak records. The peak record will have a defined upper intensity limit which, along with the instrument resolution, defines the precision with which mass will be stored. The number of bits available for storing the mass then limits the range over which the anchor mass may be used in terms of some factor of its value, so that a higher number of mass bits implies a lower number of anchors for a given precision. The anchor records can be viewed as an extraction of the exponent for the floating point representation of the mass value which can be shared by a number of peak records.

8) Further lossless compression of packed or differentiated data. A number of known compression techniques can be applied to blocks of records or entire spectra to further reduce the size of the data. Examples include many algorithms based on Lempel-Ziv and/or Huffman coding. Methods 1, 2 and 3 above often improve the performance of these algorithms by producing streams of data containing many repeating patterns. Especially when data is sparse, it can be beneficial to arrange the input data so that fields of the same type (e.g. mass index or intensity differences) lie together. It is also sometimes useful to alternate the "endian" of the binary data to increase the frequency of long strings of zeros. A simple indexing scheme may be used to recover the original spectra following decompression.

Using the library of compression methods described below, a number of preferred compression workflows can be designed to suit different needs and applications. For example:
A) Lossless compression of continuum data using methods 3, 4, 5 and 8
B) Compression of continuum data using 1-5 and 8.
C) Compression of peak-detected data using 1, 2, 6 and 7. Peak detection would be carried out after step 2.

Turning to FIGS. 2 to 5 described in specific detail is the sequence of lossless and lossy compression steps tailored to mass spectral data that can be used in many combinations, in hardware or in software, to reduce the size of the datasets produced.

2) Adaptive Thresholding.

Thresholding is a straightforward and known method of reducing the size of a dataset where only points with intensities above a predetermined threshold value are retained. A problem with this approach is that molecular species are represented in continuous mass spectra as peaks spread out over many data points. Applying a simple flat threshold to the data will often cause points which lie on the edges of peaks whose tops lie above the threshold to be discarded. This problem becomes more severe in multidimensional data (in which peaks have a width in each dimension), and in data which is well sampled (many points across a peak width).

In the method described according to an embodiment of the present invention, this problem is overcome using knowledge of peak widths. There are many possible methods that can be used to estimate the intensity (or maximum possible intensity) of a hypothetical peak at a given position in a multi-dimensional dataset. These methods include simple summation, correlation with known peak shapes and more sophisticated probabilistic approaches.

If any such calculation is performed at a sufficiently dense number of locations in the data, data points which could never contribute to a hypothetical peak exceeding some pre-determined local threshold intensity may be discarded. The local threshold intensity may vary with position in the data. The threshold intensity may be chosen using many possible criteria. For example, a minimum peak intensity may be required to achieve a predetermined minimum mass precision for a particular application.

Figure 2:
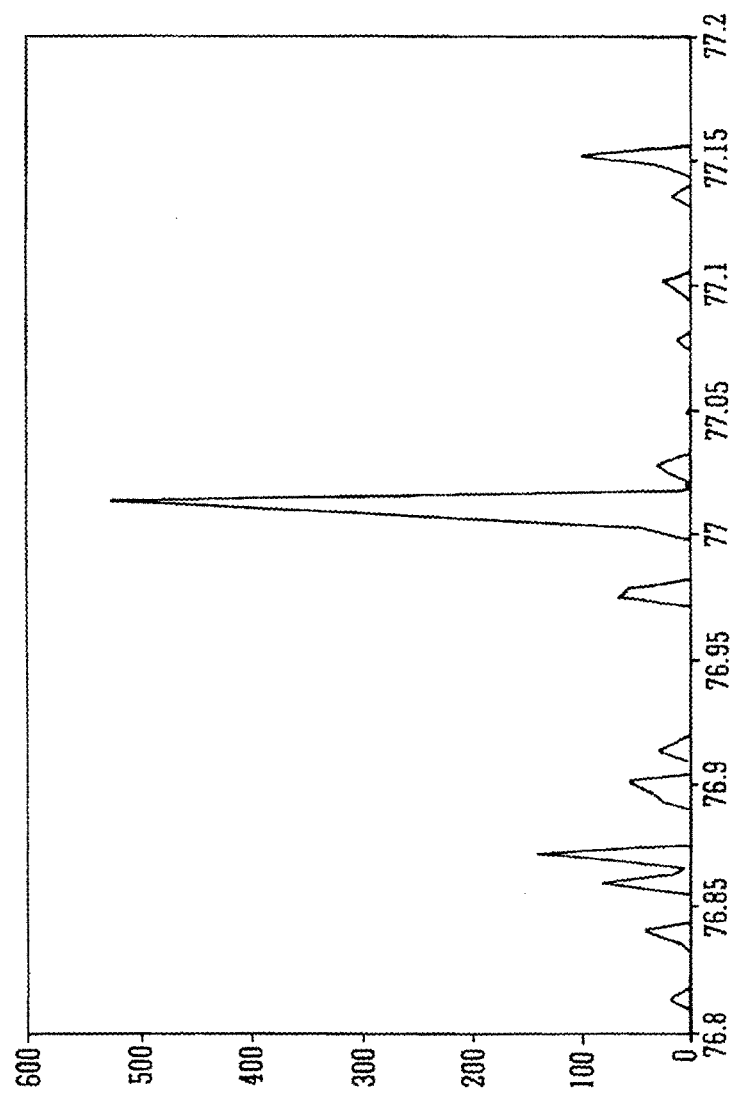
FIG. 2 is a graph of part of an uncompressed original mass spectrum.
Figure 3:
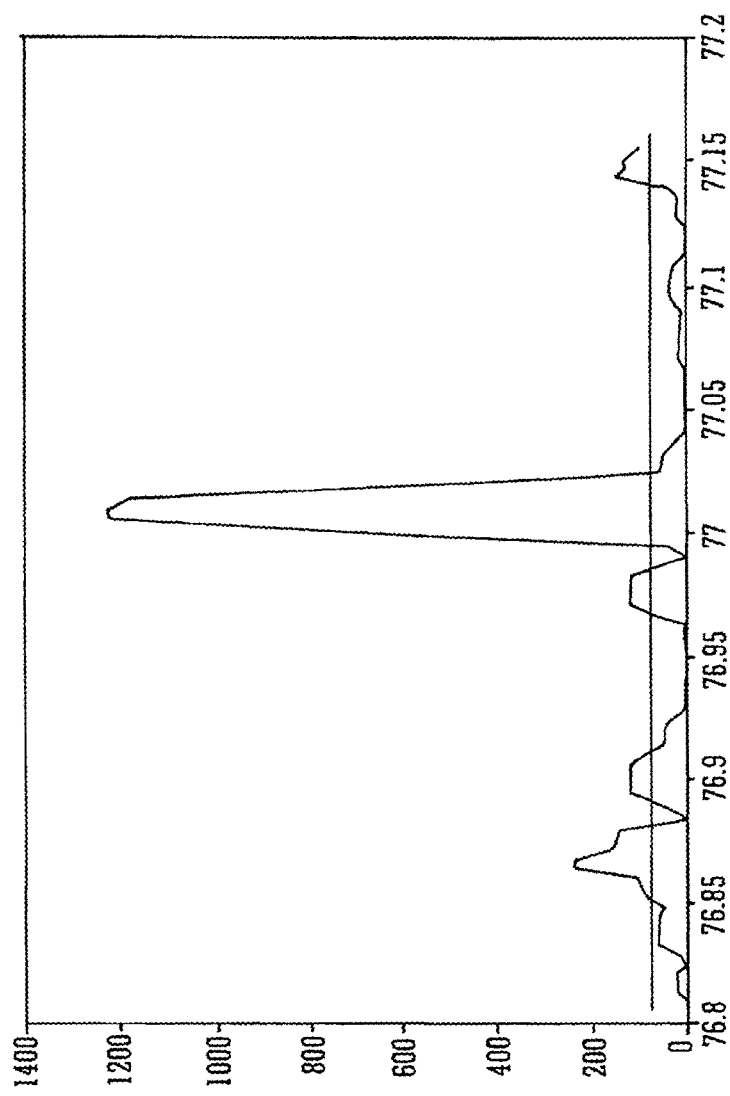
FIG. 3 is a graph of local maximum peak intensity and density threshold according to an embodiment of the invention.
Figure 4:
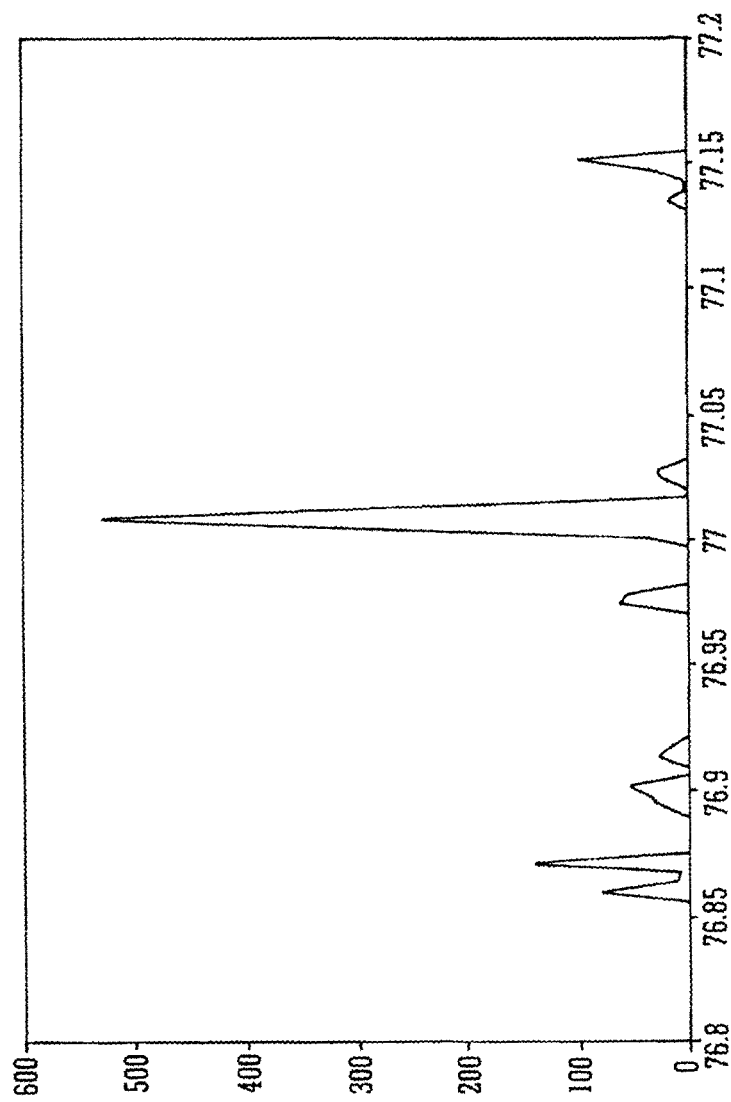
FIG. 4 is a graph of part of compressed original mass spectrum according to an embodiment of the invention.

Consider a simple one dimensional example. Part of a real mass spectrum is shown in FIG. 2. Here the x-axis is mass to charge ratio "m/z" in units Da/e and the y-axis is in arbitrary detector response units. The peak width at base is about five data points. In this example, the maximum possible intensity of a peak located at each point as the sum of the intensity of five data points centred on the point in question is estimated. This density is plotted in FIG. 3. A threshold density of 77 response units has been chosen. FIG. 4 shows the compressed spectrum in which data contributing to densities above the threshold have been retained. Notice that some points where the local density does not exceed the threshold have been retained, because they contribute to a nearby density which does lie above the threshold.

Note that this method does not necessarily rely on a particular peak detection method, but simply a method of estimating the maximum possible intensity of a hypothetical peak located at any particular point. This method may be employed in datasets of any dimensionality. A simple generalization of the one dimensional example would involve summing the intensities of points lying within a box cantered on each data point. The width of the box in each dimension would be set by the local peak width in that dimension.

This method has been successfully applied to a three dimensional LC-IMS-TOFMS (liquid chromatography, ion mobility, time of flight mass spectrometry) separation of a complex peptide mixture. Using the simple moving box method described above, and setting the threshold density at a level corresponding to approximately ten ion arrivals, the size of the dataset was reduced by a factor of around two. The width of the box was constant in the LC dimension, but varied appropriately with the width of the instrument response in the IMS and MS dimensions.

3, 4) Intensity Differentiation and Mass Differentiation

Time of flight mass spectra can be represented as a list of pairs of numbers. The first number is an integer bin index that can be mapped onto an m/z value through a calibration. It is assumed that mass indices corresponding to intensities that are zero are not stored. The second number is an intensity or "response". For peaks that are sampled appropriately (i.e. neither over-nor under-digitized), intensities in adjacent bins are correlated. In particular, the differences in intensity in consecutive bins across the peak are generally smaller than the absolute intensities. This is illustrated in the plot FIG. 5 in which the original data and differentiated data across a single peak are shown. It is evident that fewer bits will generally be required to store differences than direct intensities. Similarly, in spectra that are well populated, the differences between consecutive bin indices will generally be smaller than the original bin indices. Clearly well populated spectra are also those for which compression is most important. In the limiting case of fully populated spectra, all of the bin index differences will be 1. Again, it is evident that fewer bits will generally be required to store index differences than direct indices.

5) Intensity and Mass Difference Packing Schemes

The smaller numbers produced by mass and intensity differentiation may be exploited to reduce storage in many different ways to reduce the size of data. One method is to allocate a fixed number of bits to store a difference of each type. The number of bits allocated to store mass index or intensity differences may be chosen such that a high proportion of data points can be stored without overflow. When overflows occur, additional high precision records may be created to store either the full precision data (along with the index of the point to be repaired) or the truncated, higher order, bits.

Figure 5:
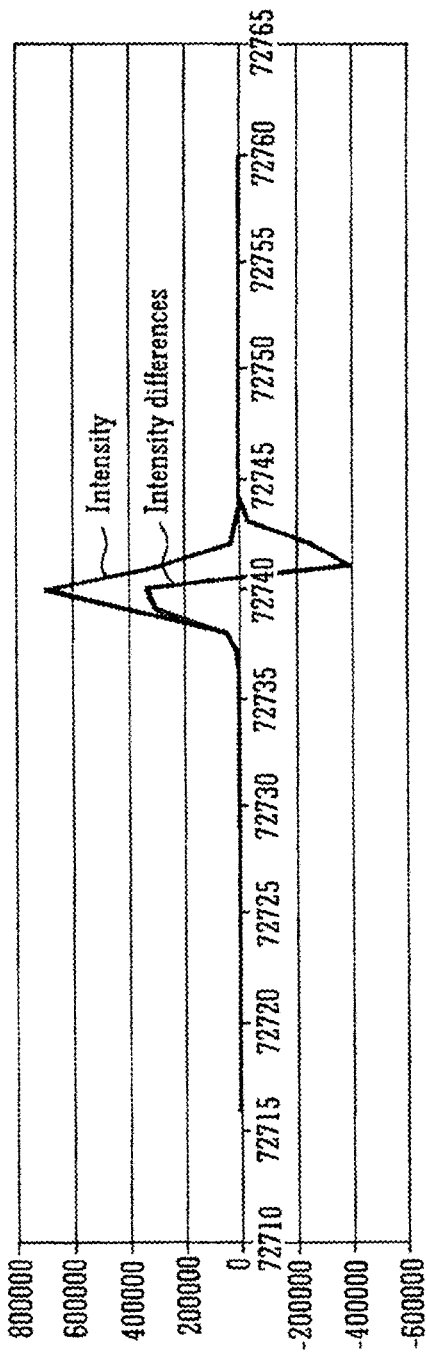
FIG. 5 is a graph of intensity and intensity differences across a single peak of a mass spectra according to an embodiment of the invention.

This is illustrated for intensities in Table 1 using the same data as FIG. 5. The intensity differences in the final column have been truncated to two bytes, and the values 5-9 are consequently incorrect.

TABLE 1

| Data Point | m/z | Intensity | Intensity Differences | Packed Intensity Differences |
|---|---|---|---|---|
| 1 | 251.8718 | 3658 | −821 | −821 |
| 2 | 251.8787 | 2593 | −1065 | −1065 |
| 3 | 251.8857 | 2179 | −414 | −414 |
| 4 | 251.8926 | 8779 | 6600 | 6600 |
| 5 | 251.8995 | 53030 | 44251 | −21285 |
| 6 | 251.9064 | 349300 | 296270 | −31410 |
| 7 | 251.9134 | 692300 | 343000 | 15320 |
| 8 | 251.9203 | 297600 | −394700 | −1484 |
| 9 | 251.9272 | 35610 | −261990 | 154 |
| 10 | 251.9341 | 4406 | −31204 | −31204 |
| 11 | 251.9411 | 825 | −3581 | −3581 |
| 12 | 251.948 | 922 | 97 | 97 |
| 13 | 251.9549 | 611 | −311 | −311 |
| 14 | 251.9619 | 367 | −244 | −244 |
| 15 | 251.9688 | 199 | −168 | −168 |

Table 2 shows the intensity difference repairs that are required for this data. In this case, the original (correct) intensities are stored directly, although the truncated high order bits could be stored instead.

When the data are read, the incorrect values are simply patched using the repair table after the data are unpacked and before the differencing is reversed

TABLE 2 intensity difference repairs

| Data point | Intensity Difference |
|---|---|
| 5 | 44251 |
| 6 | 296270 |
| 7 | 343000 |
| 8 | −394700 |
| 9 | −261990 |

Steps 3) 4) 5) and 8) were applied to 1507 blocks of 200 TOF-IMS spectra. The original, uncompressed, size of the data was 1.4 Gb, and this was reduced to 0.38 Gb after packing and encoding.

6 and 7) Efficient Packing of MS Peak Properties

The peak properties which may be packed into a binary representation are:
position (corresponds to m/z),
area (corresponds to intensity),
position error-bar,
area error-bar,
flags to indicate saturation and possible interference.

The area of a mass spectral peak is indicative of the number of ion arrivals in that region multiplied by some detector gain value. The number of ion arrivals, N, is governed by counting (e.g. Poisson) statistics, so if the gain is known, the error in using the ion count as an estimate of the underlying source strength is approximately the square root of the number of counts, $\sqrt{N}$. This suggests that peak areas can be stored as square root values without undue loss of precision as this transformation effectively equalises the precision of the stored quantity. Some low multiple (INT_SCALE) of N can be stored, so that the low bits correspond to a greater precision in $\sqrt{N}$.

INT_BITS might be available to store INT_SCALE x$\sqrt{N}$.

In time-of flight (ToF) instruments, the precision of the peak position is related to m/z divided by $\sqrt{N}$ and the resolution, $R=(m/z)/(\delta(m/z))$, where $\delta(m/z)$ is the peak width at half height. Given the resolution, the precision with which the position should be stored depends on $\sqrt{N}$. The position can be stored relative to a high precision anchor value, within some relative limit of the anchor position, REL_LIMIT. If the number of bits available to store the position is POS_BITS and assuming a maximum position resolution of R. Maximum value of $\sqrt{N}$ is $2^{\wedge}$INT_BITS/INT_SCALE, so smallest relative position error standard deviation is, RES_FACTOR/(R*$2^{\wedge}$INT_BITS/INT_SCALE), where RES_FACTOR=$(2\sqrt{2} \ln 2)^{\wedge}(-1)$, from the relationship between full width at half height and standard deviation for a Gaussian distribution.

Therefore, we need log 2((R*$2^{\wedge}$INT_BITS/INT_SCALE)/RES_FACTOR)+1 bits relative to anchor position, so, POS_BITS=INT_BITS−log 2(INT_SCALE)+log 2(REL_LIMIT*R/RES_FACTOR)+1, or, REL_LIMIT=$2^{\wedge}$(POS_BITS−INT_BITS+log 2(INT_SCALE)−1)*RES_FACTOR/R.

Embodiments of the above described techniques including a hardware module configured to implement the method of compression and the method of the invention may be used to compress data acquired from any mass spectrometer. In a preferred embodiment, the hardware module and method are used to compress data acquired from a mass spectrometer comprising an ion mobility spectrometer (IMS), and a time-of-flight (TOF) mass analyser. Such mass spectrometers may be used in series with a liquid chromatograph, as is known in the art.

Figure 6:
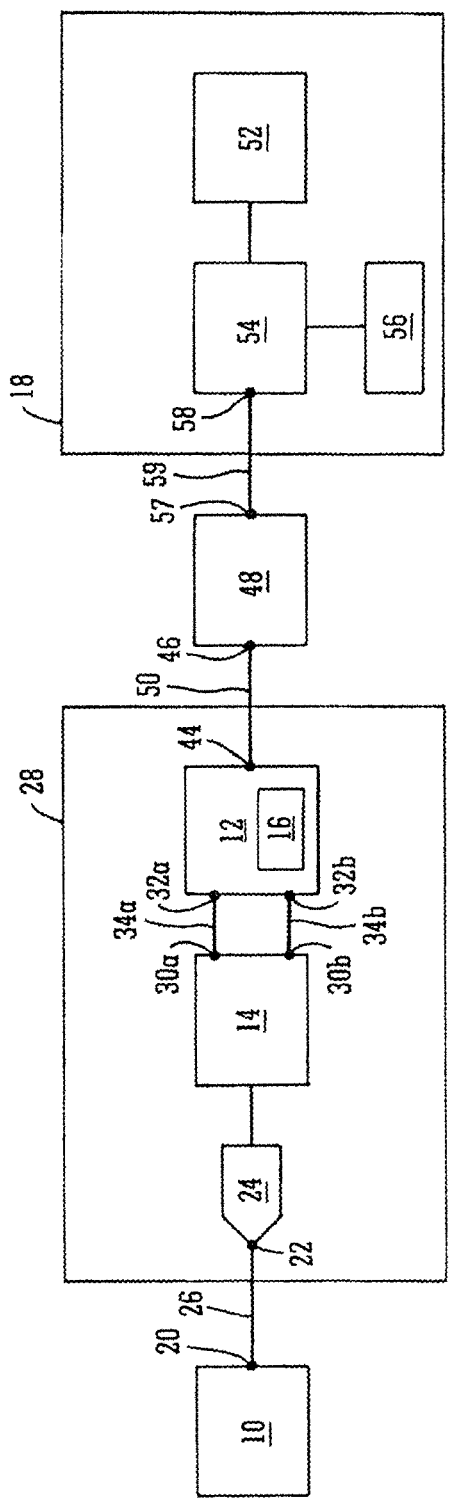
FIG. 6 is a functional block diagram of a workflow for mass spectral data analysis including a hardware module for compressing mass spectral data according to an embodiment of the invention.

Referring to FIG. 6, a functional block diagram of a workflow for mass spectral data analysis includes a hardware module for compressing mass spectral data according to an embodiment of the invention. The functional block diagram comprises a mass spectrometer 10 such as a Time of Flight mass analyser with an ion detector, an Analogue to Digital Converter (ADC) 24, signal processing and sorting logic 14 and a data processing Field Programmable Gate Array (FPGA) 12 that includes a PowerPC subsystem 16. The PowerPC subsystem 16 handles gigabit Ethernet communications with an embedded computer system 48.

More specifically, the mass spectrometer 10 has an output 20 connected to an input 22 of an analogue to digital converter 24 by an analogue signal path 26. Hardware module 28 forms the acquisition system for the mass spectrometer and comprises of the analogue to digital converter 24, signal processing and sorting logic 14 and data processing FPGA 12. The data processing FPGA 12 for compressing mass spectral data according to an embodiment of the invention is described in further detail with reference to FIG. 7. Such an arrangement is convenient for implementation in hardware such as an FPGA (Field Programmable Gate Array). The signal processing and sorting logic 14 contains two sorting algorithm logic blocks to allow parallel processing of the mass spectral data and therefore has two outputs 30a and 30b, one for each of the sorting blocks. The two outputs 30a and 30b are connected to the two inputs 32a and 32b of the data processing FPGA 12 by a pair of serial data transfer interfaces 34a and 34b. The data processing FPGA 12 has an output 44 connected to an input 46 of an embedded computer 48 by a gigabit Ethernet interface 50. The embedded computer 48 can perform further processing of the mass spectral data and also performs control functions of the mass spectrometer. It also has an output 57 connected to an input 58 of a processor core within a host computer 18 by a second gigabit Ethernet interface 59. The host computer 18 comprises a processing core 54, access to a database 52 for storing mass spectral data and a user interface 56 for control of data extraction.

It will be appreciated by a person skilled in the art, that the workflow for mass spectral data analysis can be adapted to handle multiple signals from a single detector as well as multiple signals from multiple detectors.

Figure 7:
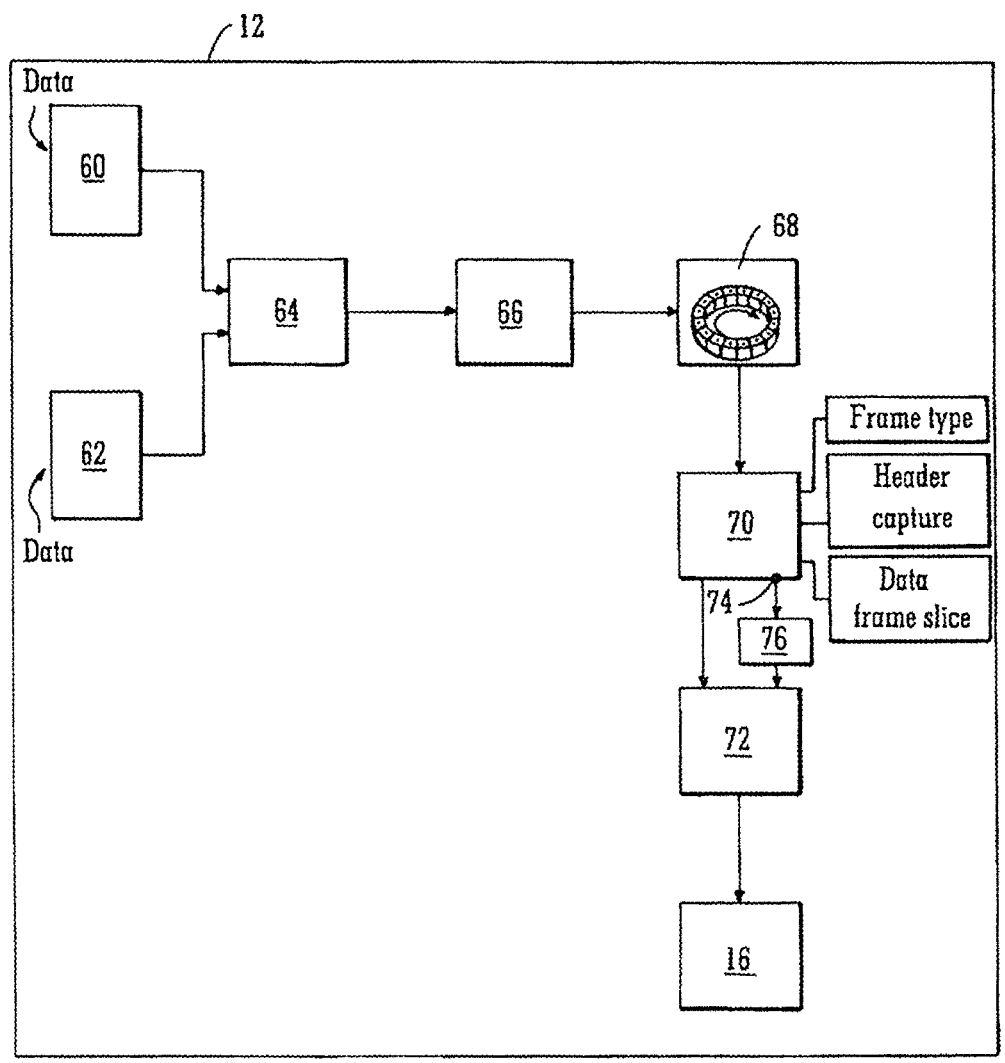
FIG. 7 is a functional block diagram of a data processing system implemented in hardware according to an embodiment of the invention.

Referring to FIG. 7, a functional block diagram of a data processing system implemented in hardware according to an embodiment of the invention comprises the hardware module 12 having a first serial data transfer interface receiver 60 and, in parallel, a second serial data transfer interface receiver 62 connected to signal processing and sorting logic (not shown in FIG. 7) which is normally configured to detect and sort peaks within the mass spectral data from a detector (via an analogue to digital convertor). Both the first serial data transfer interface receiver 60 and the second serial data transfer interface receiver 62 are herein referred to as SDTI receivers.

Both the SDTI receivers 60, 62 are connected to a scan combine module 64, the operation of which will be described in further detail below. Connected to the scan combine module 64 is a difference pipeline logic module 66 which represents a stage 1 compression of mass spectral data.

The output of the difference pipeline logic module 66 is connected to a ring buffer 68 which has an output connected to a compression control logic module 70 which represents a stage 2 compression of mass spectral data. The compression control logic module 70 has two outputs connected to an output buffer 72. One output 74 is connected to the output buffer 72 by way of a stage 3 compression of mass spectral data, in this case an LZRW3 compression stage 76.

In operation, a multiplexer selects output data from the SDTI receivers 60, 62 for normal operation. The data selected comprises of one of the following types:
Data frame
Scan statistics frame
End of read-out frame The data is then packed by combining scans and only storing intensity and mass index differences. In TOF and IMS modes, the scan combine module 64 combines the data streams from the two SDTI receivers 60, 62 into a single stream by either summation (when in TOF mode) or grouping (when in IMS mode) of the intensity values. This is to simplify the task of recombination at the host computer system end.

The difference pipeline logic module 66 compresses data frames by removing unused bits, reducing the IMS channel number from 8-bits down to a single IMS channel increment bit and converting the 24-bit absolute intensity values to 18-bit intensity difference values. It will appreciated by a person skilled in the art that the bit values described here can be different and are dependent upon the design of the mass spectrometer. To optimise the time/intensity pairs for the LZRW3 compression algorithm, it also converts the 20-bit absolute time values to 20-bit time difference values. As will be further appreciated by a person skilled in the art, other compression algorithms may require different optimisations.

As the data from the difference pipeline logic module 66 is output as bursts at a data rate that is too high for either the LZRW3 compression core or the PowerPC to cope with, the ring buffer memory 68 is used to temporarily store the packed data. The ring buffer 68 is implemented directly in the FPGA fabric for maximum performance. To the difference pipeline logic module 66, the ring buffer 68 is designed to look like a FIFO that is 32 k deep of 64-bit words. This gives a 16 segment ring buffer, each segment being a 16 kB (arranged as 2 k×64-bit words) block of RAM.

To the compression control logic module 70, the ring buffer 68 looks like a contiguous 256 kB block of memory and by using the ring buffer head and tail pointers, it can read out the next available segment when it becomes available.

As the difference pipeline logic module 66 streams the data frames into the ring buffer 68, it fills up a segment and when the segment has completely filled or an end of read-out frame is detected, the ring buffer head pointer is advanced to the next segment in the ring. Simultaneously as the compression control logic module 70 empties the ring buffer 68, the tail pointer advances around the ring. If the ring buffer 68 fills up with the head pointer catching up to the tail pointer, it throttles back the data flow from the difference pipeline logic module 66. Whenever the difference pipeline logic module 66 stops streaming data, the ring buffer 68 will continue to empty until the tail pointer catches up with the head pointer.

To determine if there is data in the ring buffer 68 that is ready to be read, the compression control logic module 70 detects a difference between the head and tail pointer numbers.

Once the compression control logic module 70 has finished processing a segment, it signals this to the ring buffer 68 which then advances the tail pointer by one towards the head pointer. If no more data is being written into the ring buffer 68 by the difference pipeline logic module 66, the tail pointer will eventually catch up with the head pointer as the ring buffer 68 empties.

As the difference pipeline logic module 66 writes new data into the ring buffer 68, the head pointer will keep advancing around the ring until it reaches the tail pointer. At this point output data will be paused until a segment is released from the tail. The ring buffer 68 can be re-initialised at any time and preferably before starting an acquisition to ensure that no spurious data has been received in the ring buffer 68.

As the compression control logic module 70 reads out the data from the ring buffer 68, it detects the type of frame, which after processing by the scan combine module 64 and difference pipeline logic module 66 can be any of the following:
Data frame
Extension data frame
Scan statistics frame
End of read-out frame Once the type of frame has been detected, any relevant fields within the frame are extracted and used to build up the header information for the output application message. If a data frame or an extension data frame is detected, the data fields are extracted and packed into a 40-bit format data frame.

For IMS mode, the 40-bit data frame is then compressed one byte at a time using the LZRW3 compression stage 76. Both compressed and uncompressed data are produced so that if the data fails to compress (as can happen as the LZRW3 compression algorithm performance is data dependent), the original uncompressed data can be used. Once all the data in the current segment has been processed as indicated by the end of the segment or the detection of an end of read-out frame, the header information is written into the header area (first 24 bytes) of the output buffer 72.

The format of the output buffer 72 format is shown below:

| Address | Function |
|---------|----------|
|         | Message & Payload Headers |
|         | Block Header - Word 1 |
|         | Block Header - Word 2 |
|         | Data block |

The output buffer 72 is organised as a two segment ring buffer and to determine if there is data in the output data buffer that is ready to be read, the application program executing on the PowerPC subsystem 16 can either use the presence of a data processing system interrupt or detect an output buffer segment ready by polling a data processing system control/status register.

As the compression control logic module 70 writes new data into the output data buffer 72, the head pointer will advance around the ring until it catches up with the tail pointer. At this point the data stream from the compression control logic module 70 will be backed off until a segment is released from the tail of the output buffer 72.

The above described hardware may be implemented, for example, in an FPGA (field programmable gate array) or in an ASIC (application specific integrated circuit) in custom silicon. Thus an embodiment provides a carrier (for example a disk such as a CD-ROM or an optical or electrical signal carrier) carrying processor control code describing such hardware. Typically hardware of this nature is described using code such as RTL (register transfer level code) or, at a higher level, for example using a language such as SystemC.

In some embodiments the hardware accelerator is implemented on a single integrated circuit.

EXAMPLE 100 ng of a cytosolic *E. coli* tryptic digest standard was injected using a nanoACQUITY system (Waters Corporation), equipped with a C18 20 mm×180 pm trap column and a C18 15 cm×75 pm analytical reversed phase column. The total gradient length was 120 minutes.

Data were acquired at a rate of 2 spectra per second using a Synapt G2-S HDMS mass spectrometer (Waters Corporation) operating at approximately 20,000 resolution (FWHM) over the m/z range 50-2000 Da/e. In both LC-MS and LC-IMS-MS experiments, the instrument was operated in a data-independent (MSE) mode and alternate low and elevated collision energy data were collected.

Lossless Compression: Differentiation, Packing and Zipping

A mass spectrum can be regarded as a pair of lists of numbers (masses and intensities). In fact, due to the digital nature of most acquisition systems, in their raw form these numbers are usually integers and shall be referred to as mass indices and intensities herein. Data points with zero intensity are usually discarded.

In a well-populated mass spectrum, consecutive mass indices often lie close together.

In the limit of a fully populated spectrum, differences between consecutive mass indices are all unity. Similarly, in well-sampled data, intensities for consecutive points are often highly correlated because the data consist of a series of peaks.

These correlations can be exploited by storing differences between consecutive mass indices and intensities in records of reduced length. As the size of the records are reduced, difference values arise that cannot be stored using the allocated record size. These overflows are stored in separate tables of repair values utilizing larger record sizes (e.g. 4 bytes).

Figure 8A:
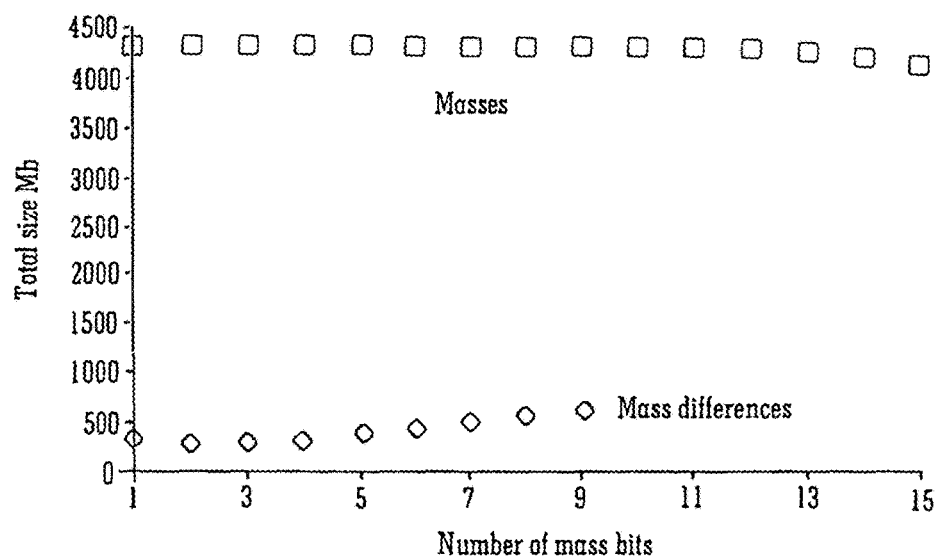
FIGS. 8A and 8B are a pair of graphs demonstrating total memory required to store the original mass index and intensity values along with the memory required to store the mass index and intensity difference and repair values arising in 120 minute LC-MS proteomics experiment.
Figure 8B:
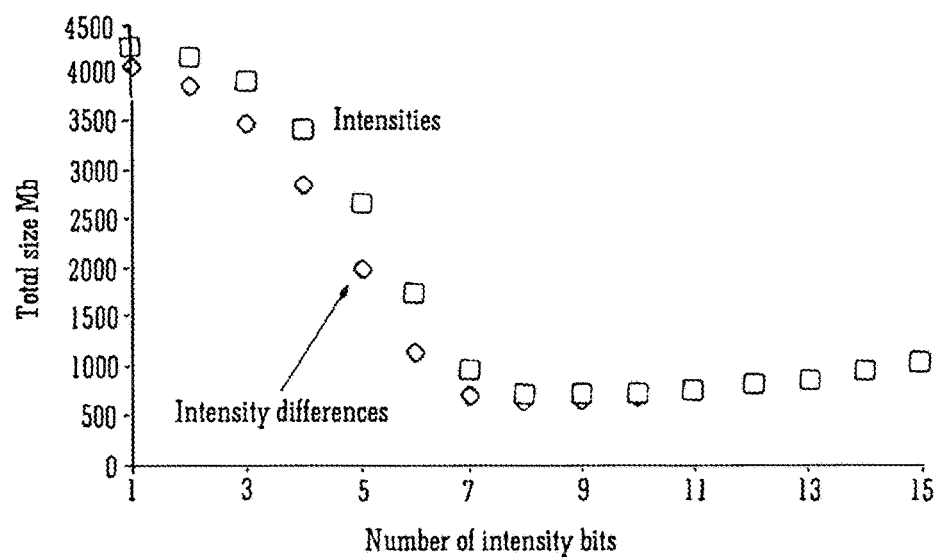

FIG. 8A shows the total memory required to store the original mass index values along with the memory required to store the mass index difference and repair values arising in a 120 minute LC-MSE proteomics experiment. FIG. 8B similarly shows the total memory required to store the original intensity values along with the memory required to store the intensity difference and repair values arising from the same experiment.

As the number of bits allocated is reduced, the size of the repair tables increases, and these eventually dominate the overall size of the data. In this example, the optimum record size is under 3 bits for mass differences, and about 8 bits for intensity differences.

Finally, data that have been packed as described above can often be compressed further using general-purpose compression algorithms.

Adaptive Background Subtraction

Electrospray data often exhibit a background of broad peaks which repeat with a period of approximately IDa. These may represent charged clusters of analyte and solvent molecules, but they do not generally yield useful information. However, the peak shape changes only slowly with m/z, and it is possible to use a moving window of the data (usually about 20 Da) to construct a model of the local background peak shape which can then be subtracted from the data. This process can remove interferences from low intensity peaks that would otherwise yield little or no information.

Figure 9A:
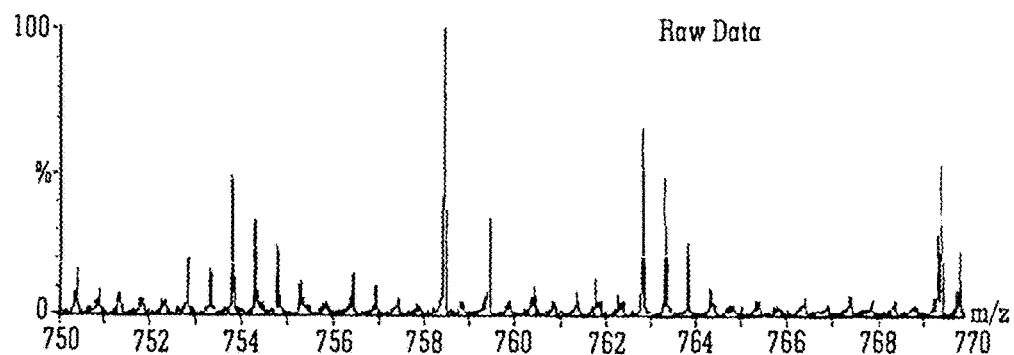
FIGS. 9A, 9B, and 9C are graphs showing a portion of mass spectrum before and after adaptive background subtraction.
Figure 9B:
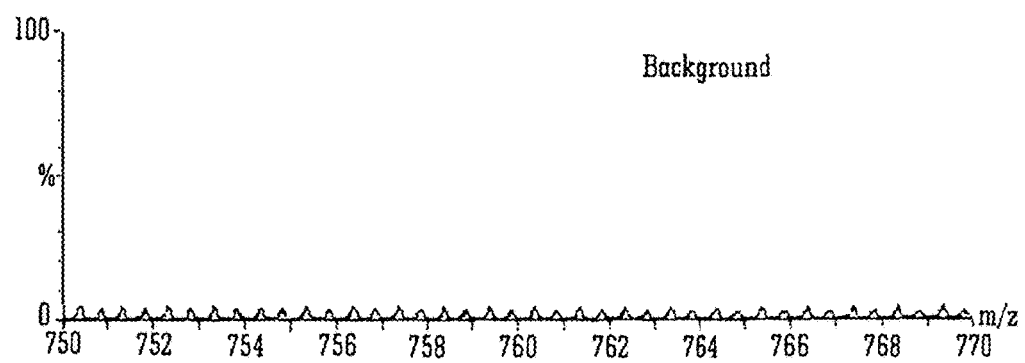
Figure 9C:
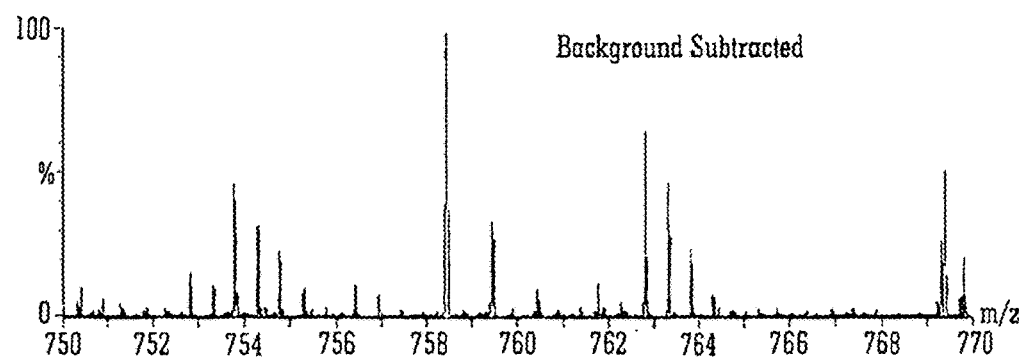

Another benefit of background subtraction is that it can substantially reduce the number of points with positive intensity in a dataset. FIGS. 8A and 8B show a portion of a mass spectrum before and after adaptive background subtraction. In this small section of spectrum, the number of points with non-zero intensity is reduced by around 45%. FIGS. 9A, 9B and 9C comprise the original data, FIG. 9A comprising 1639 points with positive intensities, while the subtracted data (FIG. 9C) has 899 points with positive intensity. The subtracted background is shown in FIG. 9B.

Data Sweep

Thresholding is a simple way to reduce the size of a dataset in which points with intensities above a pre-determined threshold value are retained. However, molecular species are represented in continuous mass spectra as peaks spread out over many data points. Applying a flat threshold to the data will often cause points which lie on the edges of peaks, whose tops lie above the threshold, to be discarded. This effect is more severe in multi-dimensional data (in which peaks have a width in each dimension), and in data which are well sampled (having many points across a peak width).

In the method described here, this problem is overcome using knowledge of local peak widths. Many methods can be used to estimate the intensity (or maximum possible intensity) of a hypothetical peak at a given position in a multi-dimensional dataset. These methods include simple summation, correlation with known peak shapes and more sophisticated probabilistic approaches.

This calculation is ideally performed at every position in the data and data points that contribute to a hypothetical peak exceeding some pre-determined local threshold intensity are labelled. Unlabelled peaks are then discarded. The local threshold intensity could vary with position in the data and might, for example, be set to achieve a minimum mass precision requirement for a particular application.

The operation of the sweep algorithm in two dimensions is illustrated schematically in FIGS. 10A and 10B. A real one dimensional example is given in FIGS. 11A, 11B and 11C in which the instrument resolution was used to set the width of the sweep window, and data points contributing to putative peaks having over 10 ion counts were retained.

Figure 11A:
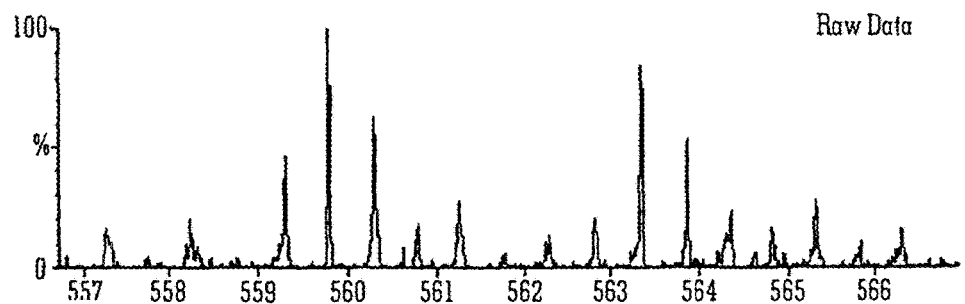
FIGS. 11A, 11B, and 11C are graphs of a mass spectrum illustrating the cumulative effect of adaptive background subtraction and data sweep.
Figure 11B:
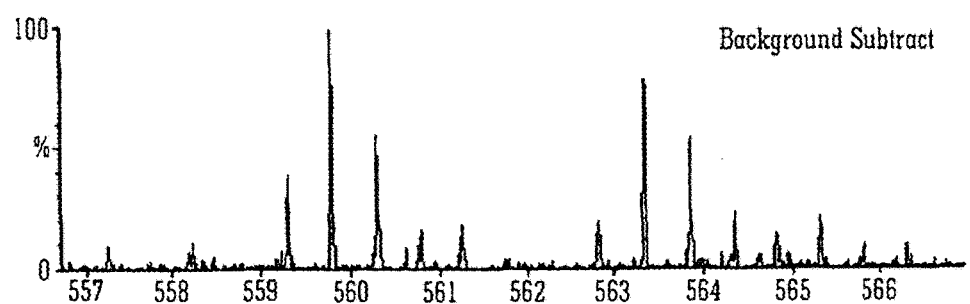
Figure 11C:
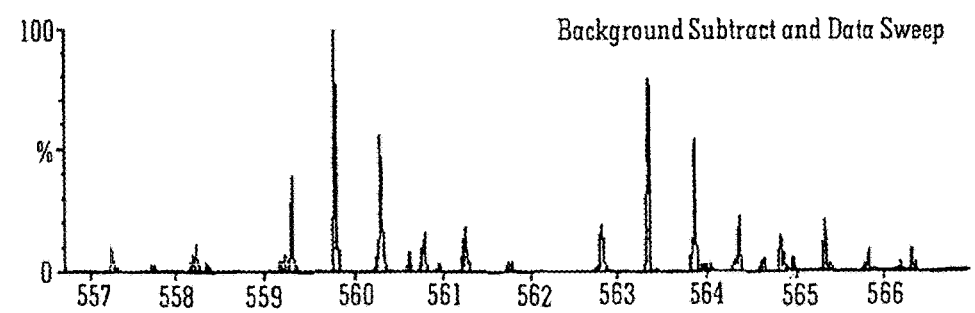

Referring to FIGS. 10A and 10B, a schematic representation of part of a 2D dataset illustrating the "Data Sweep" method of data reduction comprises spots of different sizes corresponding to datapoints with different intensities. Data point 900 is discarded, as none of the possible peak positions (some examples of which are represented by the unfilled circles) correspond to peaks of above-threshold intensity. The point labelled 902 is retained due to a higher local density of data. As best seen in FIGS. 11A-C, part of a mass spectrum illustrating the cumulative effect of adaptive background subtraction and data sweep comprises original data (FIG. 11A), and data following background subtraction (FIG. 11B). FIG. 11C shows the data following a one dimensional data sweep.

Results

The original and compressed forms of the LC-MSE dataset were processed and searched using ProteinLynx Global Server version 2.5.2. Ion detection thresholds were lowered for processing of background subtracted data, but otherwise processing parameters were identical. The requested false positive rate was 4%. The results are presented in Table 3 and Table 4 below. In both cases the "Original" size refers to the native raw file format produced by the instrument.

TABLE 3

| LC-MSE | Original | ABS | +Sweep | +Lossless |
| --- | --- | --- | --- | --- |
| Low Energy | 5109 Mb | 4669 Mb | 2647 Mb | 531 Mb |
| Elev. Energy | 5033 Mb | 4649 Mb | 2184 Mb | 406 Mb |
| Total | 10142 Mb | 9318 Mb | 4831 Mb | 937 Mb |
| Protein ID's | 684 | 667 | 664 | 664 |

TABLE 4

| LC-IMS-MSE | Original | ABS | +Lossless |
| --- | --- | --- | --- |
| Low Energy | 9572 Mb | 4856 Mb | 1465 Mb |
| Elev. Energy | 10514 Mb | 5313 Mb | 1617 Mb |
| Total | 20086 Mb | 10166 Mb | 3082 Mb |
| Proteins ID's | 823 | 851 | 851 |

The results indicate that useful compression of electrospray time-of-flight MS datasets is possible without significant loss of data quality. In particular, over ten-fold compression of the LC-MSE dataset is achieved. At the same time, no statistically significant decrease in the number of proteins identified is observed. Interestingly the final, lossless compression step delivers the largest compression ratio.

No doubt other effective alternatives will occur to the skilled person. It will be understood that the invention is not limited to the described embodiments and encompasses modifications apparent to those skilled in the art lying within the scope of the claims appended hereto.

The invention claimed is:

1. A method of compressing mass spectral data, the method comprising:
   receiving a first signal output from an ion detector of a mass spectrometer;
   processing the first signal to a digital signal at an output being one or more data frames representative of the first signal output;
   temporarily storing the one or more data frames in a memory block; and
   reading a data frame from the memory block and determining a data frame type of the data frame and according to the data frame type compressing the data frame according to one or more compression algorithms to generate a compressed data output stream, wherein the one or more compression algorithms include:
   providing intensity or m/z information in respect of a first data point by calculating the difference between the intensity of the first data point and an intensity of a second data point adjacent the first data point or by calculating the difference between a mass index or m/z of the first data point and a mass index or m/z of a second data point adjacent the first data point;
   performing further compression, wherein the further compression is lossless;
   determining an intensity distribution from a plurality of different regions or portions of mass spectral data or of a mass spectrum;
   constructing a model of a local background peak shape for one or more regions or portions of said mass spectral data or said mass spectrum from said intensity distribution; and
   adjusting an intensity of one or more regions or portions of said mass spectral data or said mass spectrum based on the constructed model of the local background peak shape in order to remove or reduce the effects of an estimated background intensity.

2. A method as claimed in claim 1, wherein the step of processing the first signal to a digital signal comprises using an analogue to digital converter to digitise the first signal.

3. A method as claimed in claim 1, wherein the method is carried out in real time.

4. A method as claimed in claim 1, wherein the method is carried out on previously acquired mass spectral data.

5. A method as claimed in claim 1, wherein the data frame type is any one of a data frame, scan statistics frame and read-out frame.

6. A method as claimed in claim 1, wherein the first signal output is a voltage or representative of one or more ion arrival times or one or more ion intensities.

7. A method as claimed in claim 1, wherein performing further compression comprises performing Lempel-Ziv or Huffman coding.

8. A computer software program for implementing the method claimed in claim 1.

9. A carrier carrying processor control code to configure hardware to implement the method as claimed in claim 1.

10. A hardware module configured to implement the method of compression as claimed in claim 1.

11. A hardware module for compressing mass spectral data, the hardware module comprising:
an input to receive input data being a first signal output from an ion detector, the data being characteristic of ion arrival times or ion intensities;
an analogue to digital converter, to receive at the input the first signal and process the first signal to a digitised first signal;
a first processor block, the first processor block having logic gates to receive the digitised first signal and process the first signal to one or more data frames;
a second processor block comprising a buffer having an input to receive the one or more data frames and a memory block to temporarily store the one or more data frames and an output coupled to a compression control logic block for reading a data frame from the memory block and for determining a data frame type of the data frame and according to the data frame type compressing the data frame according to one or more compression algorithms to generate a compressed data output stream, wherein the one or more compression algorithms include:
providing intensity or m/z information in respect of a first data point by calculating the difference between the intensity of the first data point and an intensity of a second data point adjacent the first data point or by calculating the difference between a mass index or m/z of the first data point and a mass index or m/z of a second data point adjacent the first data point; and
performing further compression, wherein the further compression is lossless;
determining an intensity distribution from a plurality of different regions or portions of mass spectral data or of a mass spectrum;
constructing a model of a local background peak shape for one or more regions or portions of said mass spectral data or said mass spectrum from said intensity distribution; and
adjusting an intensity of one or more regions or portions of said mass spectral data or said mass spectrum based on the constructed model of the local background peak shape in order to remove or reduce the effects of an estimated background intensity.

12. A hardware module as claimed in claim 11, wherein first signal output is a voltage or representative of one or more ion arrival times or one or more ion intensities.

13. A hardware module as claimed in claim 11, wherein the first processor block may comprise multiple processing blocks to allow parallel processing of the digitised first signal.

14. A hardware module as claimed in claim 11, wherein the second processor block may comprise a scan combine logic block for combining multiple data streams from the first processor block into a single data stream by summation or grouping of the intensity values.

15. A hardware module as claimed in claim 11, wherein the compression control logic block performs the compressing in real time, for example using a Field Programmable Gate Array ("FPGA") or a Graphical Processor Unit ("GPU").

16. A mass spectrometer comprising a hardware module according to claim 11.

17. A method of compressing ion mobility data, the method comprising:
receiving a first signal output from an ion detector of an ion mobility spectrometer;
processing the first signal to a digital signal at an output being one or more data frames representative of the first signal output;
temporarily storing the one or more data frames in a memory block; and
reading a data frame from the memory block and determining a data frame type of the data frame and according to the data frame type compressing the data frame according to one or more compression algorithms to generate a compressed data output stream, wherein the one or more compression algorithms include:
providing intensity or ion mobility information in respect of a first data point by calculating the difference between the intensity of the first data point and an intensity of a second data point adjacent the first data point or by calculating the difference between an ion mobility index or ion mobility of the first data point and an ion mobility index or ion mobility of a second data point adjacent the first data point; and
performing further compression, wherein the further compression is lossless;
determining an intensity distribution from a plurality of different regions or portions of mass spectral data or of a mass spectrum;
constructing a model of a local background peak shape for one or more regions or portions of said mass spectral data or said mass spectrum from said intensity distribution; and
adjusting an intensity of one or more regions or portions of said mass spectral data or said mass spectrum based on the constructed model of the local background peak shape in order to remove or reduce the effects of an estimated background intensity.

18. A hardware module for compressing ion mobility data, the hardware module comprising:
an input to receive input data being a first signal output from an ion detector, the data being characteristic of ion arrival times or ion intensities;
an analogue to digital converter, to receive at the input the first signal and process the first signal to a digitised first signal;
a first processor block, the first processor block having logic gates to receive the digitised first signal and process the first signal to one or more data frames;
a second processor block comprising a buffer having an input to receive the one or more data frames and a memory block to temporarily store the one or more data frames and an output coupled to a compression control logic block for reading a data frame from the memory block and for determining a data frame type of the data frame and according to the data frame type compressing the data frame according to one or more compression algorithms to generate a compressed data output stream, wherein the one or more compression algorithms include:
providing intensity or ion mobility information in respect of a first data point by calculating the difference between the intensity of the first data point and an intensity of a second data point adjacent the first data point or by calculating the difference between an ion mobility index or ion mobility of the first data point and an ion mobility index or ion mobility of a second data point adjacent the first data point; and
performing further compression, wherein the further compression is lossless;

determining an intensity distribution from a plurality of different regions or portions of mass spectral data or of a mass spectrum;

constructing a model of a local background peak shape for one or more regions or portions of said mass spectral data or said mass spectrum from said intensity distribution; and adjusting an intensity of one or more regions or portions of said mass spectral data or said mass spectrum based on the constructed model of the local background peak shape in order to remove or reduce the effects of an estimated background intensity.

* * * * *